United States Patent [19]

Goldowsky

[11] Patent Number: 4,759,130
[45] Date of Patent: Jul. 26, 1988

[54] GONIOMETER HEAD ARRANGEMENT

[75] Inventor: Michael Goldowsky, Valhalla, N.Y.

[73] Assignee: U.S. Philips Corporation, New York, N.Y.

[21] Appl. No.: 36,134

[22] Filed: Apr. 6, 1987

Related U.S. Application Data

[63] Continuation of Ser. No. 797,105, Nov. 12, 1985, abandoned.

[51] Int. Cl.$^4$ ............................................. G01B 11/26
[52] U.S. Cl. .................................... 33/1 N; 33/534; 125/30 R; 356/30
[58] Field of Search ............ 33/1 N, 534, 573, 164 B, 33/475; 356/30, 31, 138, 154, 244; 125/30 R, 35; 378/79, 81

[56] References Cited

U.S. PATENT DOCUMENTS

| 2,858,730 | 11/1958 | Hanson | 125/30 R |
| 3,600,576 | 8/1971 | Carter | 378/81 |
| 4,065,211 | 11/1983 | Vig | 356/31 |
| 4,071,758 | 1/1978 | Steinbichler | 378/81 |
| 4,417,564 | 12/1977 | Lawrence et al. | 356/30 |
| 4,543,724 | 10/1985 | Shiba et al. | 33/1 N |

FOREIGN PATENT DOCUMENTS

| 2009642 | 6/1979 | United Kingdom . | |
| 2074480 | 11/1981 | United Kingdom | 356/30 |

Primary Examiner—William A. Cuchlinski, Jr.
Assistant Examiner—Patrick R. Scanlon
Attorney, Agent, or Firm—Paul R. Miller

[57] ABSTRACT

A unique and novel goniometer is set forth to orient a sample in an X-ray beam, for example, to better than 0.001° without introducing translation. This structure is infinitely adjustable and stable.

2 Claims, 2 Drawing Sheets

GONIOMETER HEAD ARRANGEMENT

This is a continuation of application Ser. No. 797,105, filed Nov. 12, 1985 and now abandoned.

The present invention relates to a new and unique goniometer head for orienting a sample with respect to an X-ray beam with an accuracy of better than 0.001° without introducing translation, as well as to be infinitely adjustable and stable.

Various commercially available goniometers have been used over the years, together with special designs for positioning crystals or other samples in X-ray diffractometers, for example. Such prior goniometers are sufficiently accurate for typical positioning to 0.01°.

In a new type of biaxial diffractometer recently achieved, positioning accuracy is required of a value ten times better than that previously achieved. Typically, positioning accuracy values of 0.001° are necessary in this new biaxial diffractometer, and the previously available goniometers have been found to be inadequate to position samples to this resolution. Moreover, once a setting is locked into position, angular position of the goniometer is ordinarily not sufficiently stable. In fact in some of the prior designs, the sample is forced to translate when angular adjustments are made. This is undesirable for small samples since they could move out of the X-ray beam. Also, typical goniometers employ relative sliding members, such as bearings and linear slides, which have unacceptable clearances and are difficult to preload. Such mechanisms do not exhibit good long-term stability.

The present invention provides a new, unique goniometer avoiding all previous difficulties.

The present invention eliminates all clearances, bearing structures, etc. by creating an angular deflection in a cantilever rod. By imposing a force to the rod at a correct location, translation of the sample can be made zero.

This new design and construction for a goniometer achieves high resolution with mechanical stability of angular adjustments, which finds wide application. Goniometer heads are commonly used to adjust mirrors in optical systems and the advantages of the present invention also find significant applicability in such systems.

The structure and advantages of this new goniometer can be seen without limitation in the attached drawing figures, in which.

Figure 1:
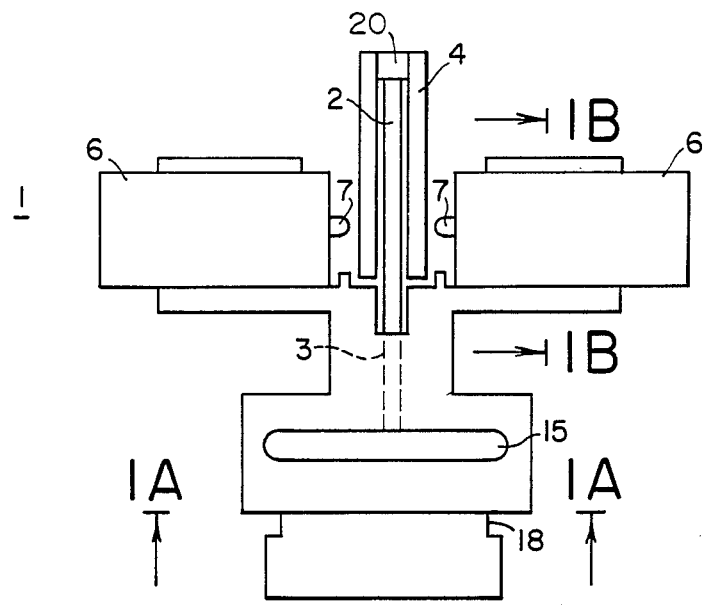
FIG. 1 illustrates in side elevational view the new goniometer of the present invention.

In FIG. 1 a cross-sectional view of the goniometer 1 according to the present invention is set forth with a cantilever rod 2 mounted to be cantilevered out of the top of a lead screw 3. The cantilever rod 2 has a sample mount 20 located at the top end. The lead screw 3 adjusts vertical height of the cantilever rod 2. A rigid cylinder 4 is attached to the top of the rod 2 and surrounds it over a significant position of its length. Typically, the rod may have a diameter of 0.062 inches with a length of 1.06 inches, and a force P will be applied to the rigid cylinder at a distance from the top of approximately two-thirds the length of the cantilever rod 2. An angular movement of $\theta$ can then be achieved for the cantilever rod 2.

The application of a force P to the rigid cylinder 4 at a distance L from the top of the cantilever rod 2 will result in a bending moment, $P \times L$, on the rod 2. This moment bends the rod 2 in a direction so that no net translation from the axis of the rod takes place for the rod end 5, as may be seen in FIG. 2B. Only angular deflection at an angle $\theta$ will take place at the end 5 of the rod.

Figure 2A:
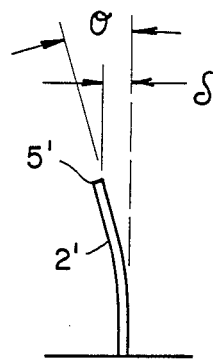
FIG. 2A illustrates the normal cantilever action according to the prior art.
Figure 2B:
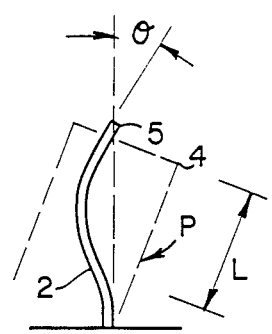
FIG. 2B illustrates the deflection according to the present invention.

This is distinctive from the deflection of a standard cantilever rod 2, such as seen in FIG. 2A, having a load P applied at its end 5'. The end 5' translates an amount $\delta$ and rotates at an angle $\theta$ away from the central position of the standard cantilever rod. Thus, the translation $\delta$ moves the end 5' of the normal cantilever rod 2' from the center axis of the cantilever rod.

On the other hand, by the construction of the present invention only angular deflection at the end 5 of the rod 2 will take place. It has been found that if the length L is chosen to be about two-thirds of the length of the cantilever rod 2, then the condition of zero translation will occur so that only angular deflection occurs with this new cantilever rod without displacement.

The elimination of moving parts is a major advantage for achieving long-term stability of the mounting structure. By the choice of proper dimensions, the stress level in the rod 2 is low and a long-term stability is ensured.

Figures 1A, 1B:
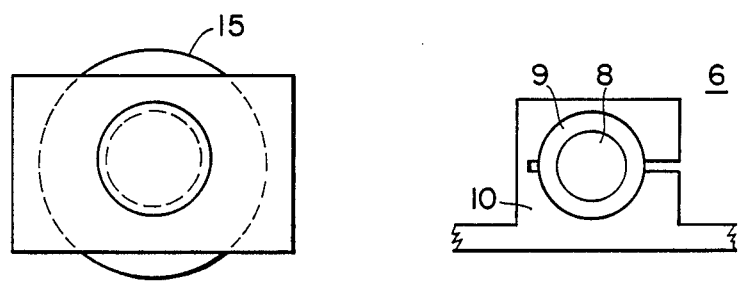
FIG. 1A illustrates a cross-sectional view through portion A—A in FIG. 1.
FIG. 1B illustrates a cross-sectional view through position B—B in FIG. 1.
Figure 3:
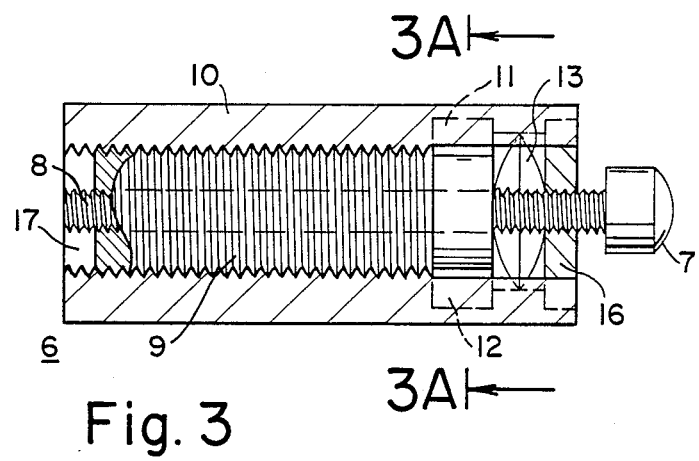
FIG. 3 illustrates construction of a portion of the present invention.

The adjustment of the goniometer structure 1 occurs by way of the actuator structures as seen in FIGS. 1, 1B and 3. Four actuators 6 are placed at 90° from one another around the rigid cylinder 4. By appropriate adjustment of these actuators, as will be discussed relative to FIG. 3, opposite pairs of the actuators 6 are used to lock the cylinder into position after adjustment. This occurs by way of the rounded tips 7 at the ends of the actuator 6. These rounded tips 7 push on a hardened flat area of the rigid cylinder 4 so that stable orthogonal adjustment is possible.

FIG. 3 shows the construction of one actuator 6 having a central screw 8 with a standard metric thread. This central screw 8 is threaded into a surrounding screw 9 which uses an English thread. The larger screw 9 is threaded into the housing 10 of the actuator 6 so that when the large screw is rotated one turn, the central screw 8 advances by the difference in the pitch. This small advancement by the difference in pitch is significantly more sensitive than a common micrometer.

As an example, in the use of a metric thread of 0.50 mm pitch for the central screw 8, and an English thread of 48 threads per inch (0.53 mm pitch) for the surrounding screw 9, then advancement of one turn of the surrounding larger screw 9 advances the inner central screw 8 by 0.3 mm (0.0012 inches or 1.2 mils.). This 1.2 mils. of displacement per turn of the large surrounding screw 9 is 25 times more sensitive then the common micrometer. For approximately 5° of screw rotation, the angular change will be 0.001°.

This easily meets the design constraint of the present invention with good operator "feel". Although the smaller central screw advances only 1.2 mils. per turn, the larger surrounding screw 9 advances 20.8 mils. The actuator housing 10 must be sufficiently long to accommodate this travel.

Figure 3A:
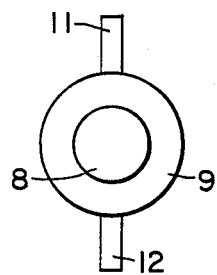
FIG. 3A illustrates a cross-sectional view through position A—A of FIG. 3.

The central screw 8 is kept from rotating by engagement of an attached key 11, 12 shown in FIG. 3A. This key engages slots in the housing 10 with a 1 to 3 mil. clearance to prevent rotation of the central screw 8. A preloading by a combination of flat and wavy washers 13 is provided on both screw threads by a press fit bearing 16 so as to remove backlash and make adjustment more stable.

The actuator 6 may be adjusted by using a special tool (not shown) that engages a slot 17 in the end of the screw 9 to turn the tip 14. The tool is hollow in order to be inserted over screw 8.

The construction of the goniometer is further provided by a vertical adjustment of the rod 2 by the lead screw 3 shown in FIG. 1. This is accomplished by using a captivated nut 15, which is exposed at least at one side as seen in FIG. 1A. The nut 15 engages the lead screw 3. A keyed fitting 18 is locked into position with set screws (not shown).

What I claim:

1. A goniometer head arrangement comprising a cantilevered rod having a length extending along a longitudinal axis, a rigid housing surrounding said rod, said housing being attached to a free end of said rod, and means for applying a force to said housing at a position approximately two-thirds of the length of said rod from said free end, said free end maintaining a position on said longitudinal axis.

2. A goniometer head arrangement according to claim 1, wherein an opposite end of said rod is adjustably mounted for movement of said rod along said longitudinal axis.

* * * * *